US 6,517,582 B2

United States Patent
Willi et al.

(10) Patent No.: US 6,517,582 B2
(45) Date of Patent: Feb. 11, 2003

(54) BALL DRAW-OFF APPARATUS FOR SHAFT PROSTHESES

(75) Inventors: Thomas Willi, Breite Nuerensdorf (CH); Ines Baum, Konstanz (DE)

(73) Assignee: Sulzer Orthopedics Ltd., Bear (CH)

( * ) Notice: Subject to any disclaimer, the term of this patent is extended or adjusted under 35 U.S.C. 154(b) by 16 days.

(21) Appl. No.: 09/900,318

(22) Filed: Jul. 6, 2001

(65) Prior Publication Data

US 2002/0004684 A1 Jan. 10, 2002

(30) Foreign Application Priority Data

Jul. 7, 2000 (EP) ............................................. 00810596

(51) Int. Cl.$^7$ ................................................. A61F 2/46
(52) U.S. Cl. .................................................. 623/22.12
(58) Field of Search .................. 606/99, 100; 623/22.16, 623/22.12

(56) References Cited

U.S. PATENT DOCUMENTS

| 3,801,989 A | | 4/1974 | McKee | |
| 5,196,018 A | * | 3/1993 | Willert et al. | 606/100 |
| 5,264,680 A | * | 11/1993 | Seibold et al. | 219/221 |

FOREIGN PATENT DOCUMENTS

| DE | 4441870 C1 | 3/1996 |
| WO | WO 93/02642 | 2/1993 |

* cited by examiner

*Primary Examiner*—Nicholas D. Lucchesi
*Assistant Examiner*—Fenn Mathew
(74) *Attorney, Agent, or Firm*—Townsend and Townsend and Crew LLP

(57) ABSTRACT

The invention relates to a ball draw-off apparatus for shaft prostheses with balls (3) which can be placed onto the prosthesis neck (2). The apparatus has two rotary bodies (5a, 5b) which are rotatably supported in a housing (4), which can in each case be rotated with a lever arm (6a, 6b) and which with their axes of rotation (7a, 7b) lie in a common plane and form an open gap S in the projection onto the plane F for the introduction of the prosthesis neck (2). The rotary bodies have a profile which with increasing rotation decreases the gap S for clamping the prosthesis neck (2) and causes an increase of the distance of its upper edge (9a, 9b) from the plane F in order to produce a draw-off force P at the placed on ball directly or indirectly via an intermediate body.

14 Claims, 5 Drawing Sheets

Figure 1:
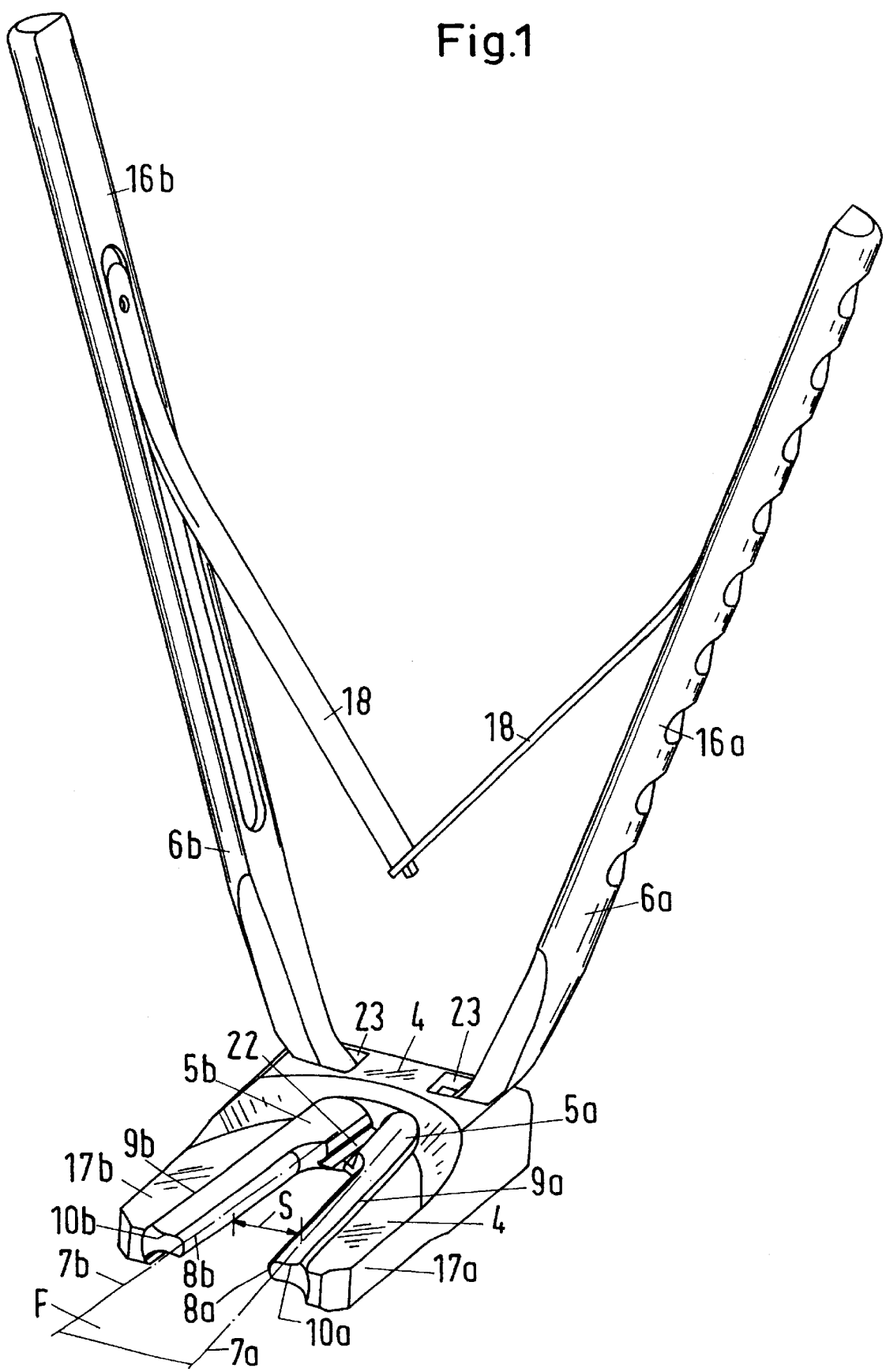

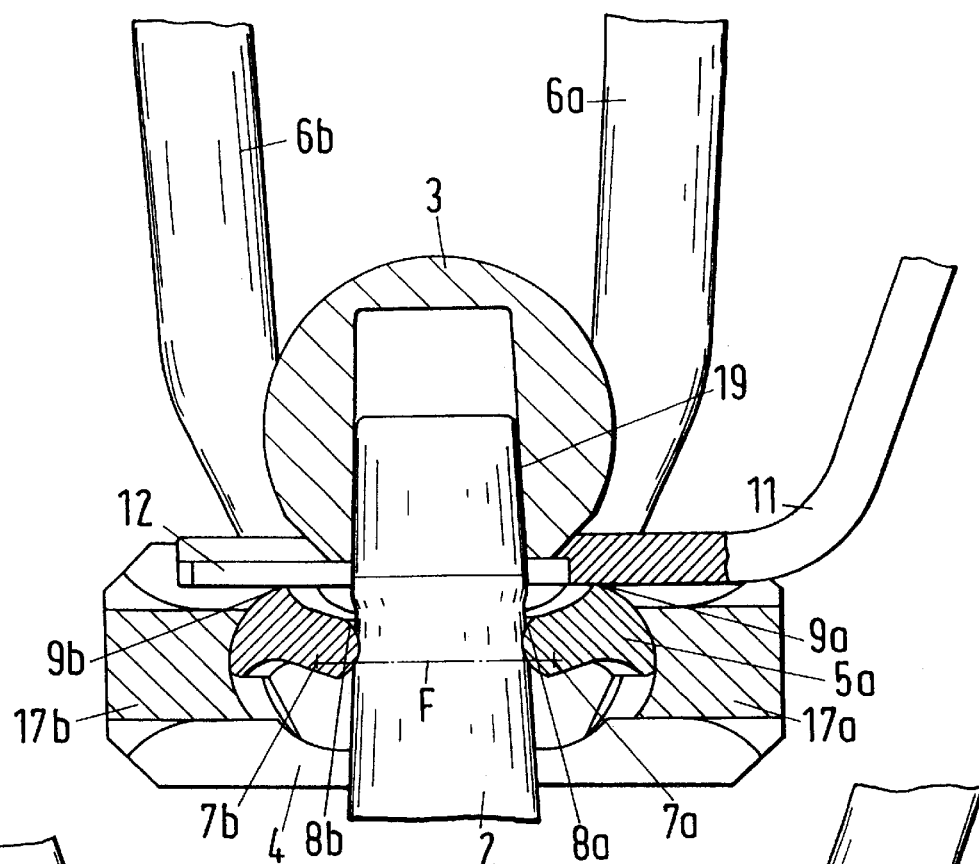
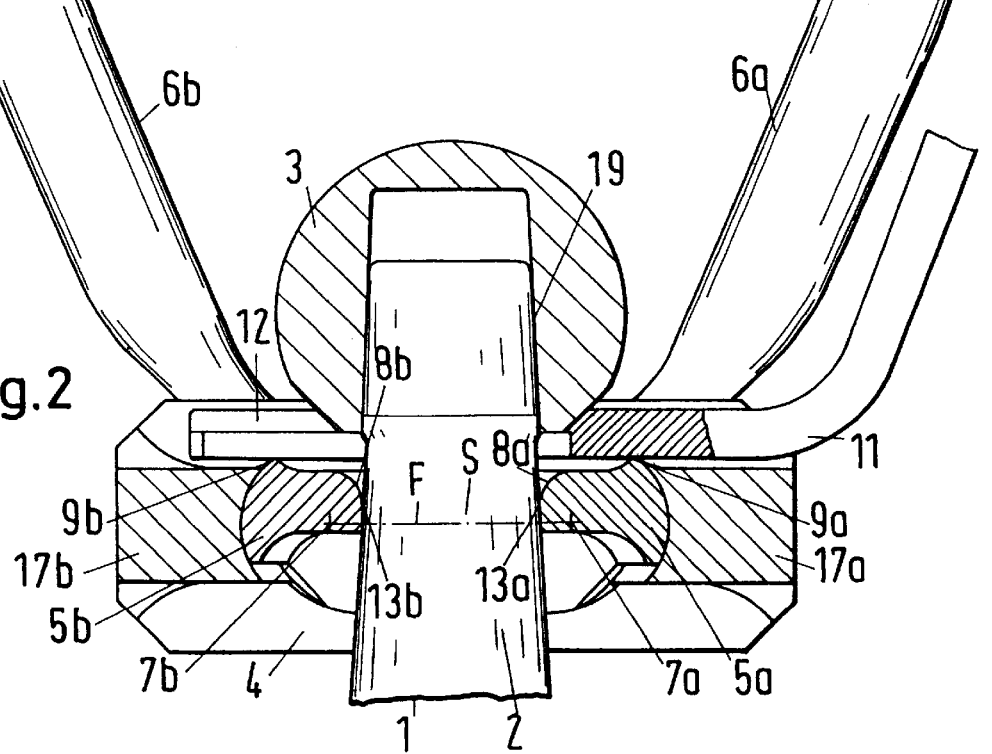

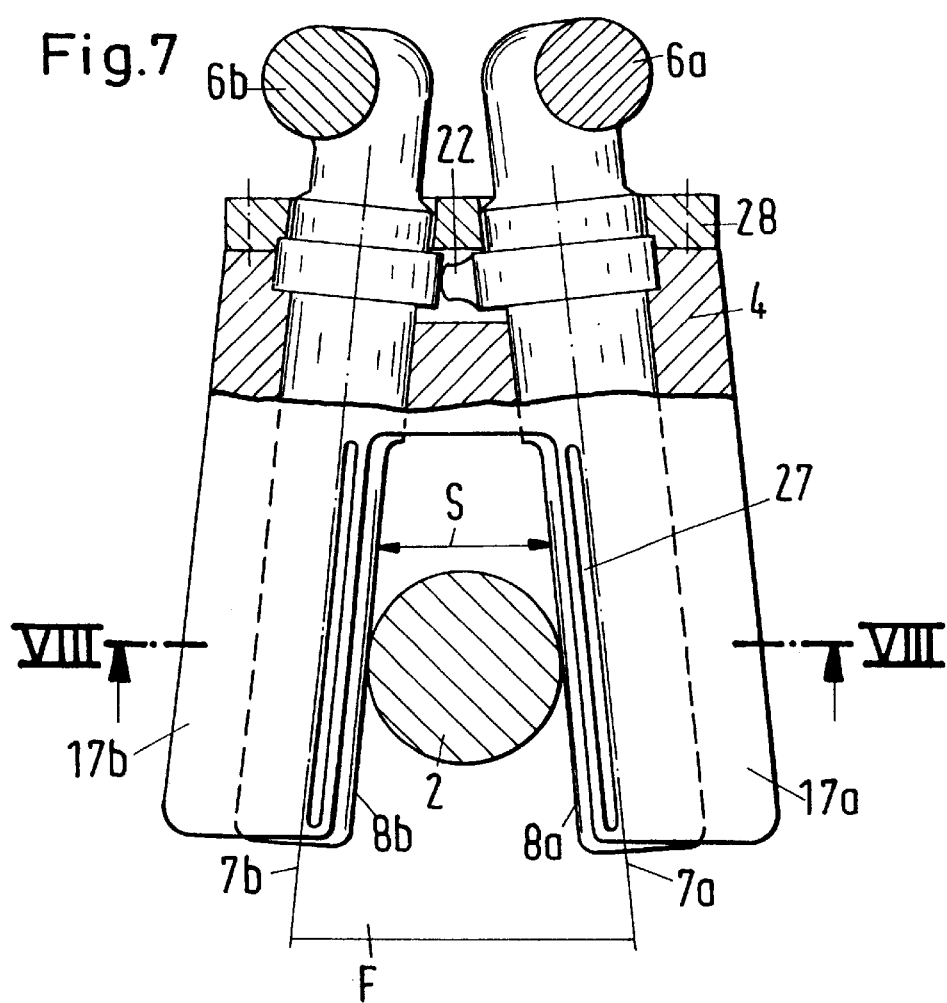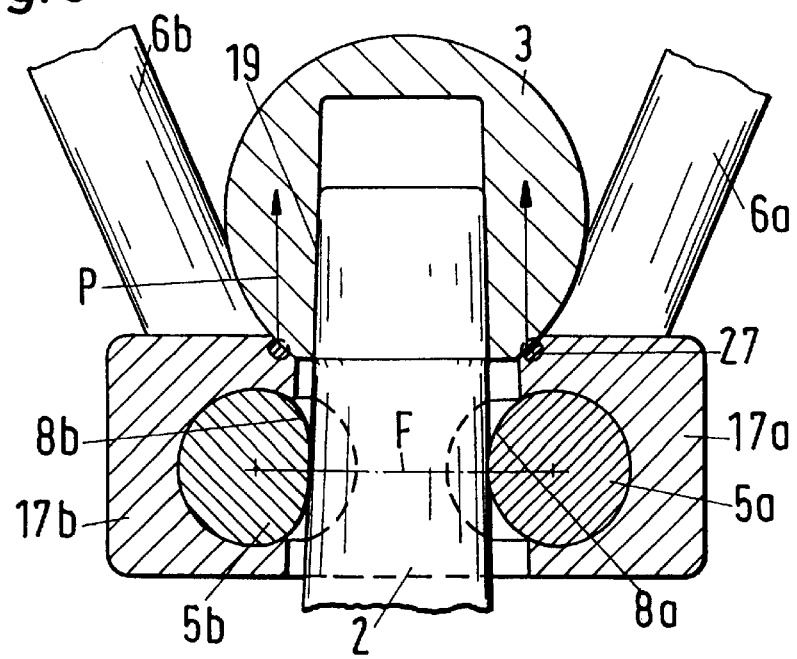

BALL DRAW-OFF APPARATUS FOR SHAFT PROSTHESES

The invention relates to a ball draw-off apparatus for shaft prostheses with balls which can be placed onto the prosthesis neck.

In re-operations of hip joints it occurs that a femur shaft is still anchored so well that a new shaft is not necessary. In such a case it is sufficient to remove the joint ball from the prosthesis shaft and to place on a new joint ball, which for example is combined with a completely new acetabulum.

Up to now joint balls, which are placed on with a conical press fit on a femur shaft, were grasped by an auxiliary tool and removed through cautious hammering out with a sliding hammer. This hammering out at a shaft which is intact and anchored in the bone represents an unnecessary risk for a loosening of the shaft, since the adhesion of the ball on the shaft can not be predicted exactly.

The object of the invention is to create simple instruments which ensure a careful removal of the ball. This is achieved in that the apparatus has two rotary bodies which are rotatably supported in a housing, which can in each case be rotated with a lever arm and which lie with their axes of rotation in a common plane and form an open gap S in the projection onto the plane F for the introduction of the prosthesis neck, with the rotary bodies having a profile which with increasing rotation decreases the gap S for clamping the prosthesis neck and causes an increase of the distance of its upper edge from the plane F in order to produce a draw-off force P at the placed on ball directly or indirectly via an intermediate body.

The advantage of this apparatus lies in that it can be used for the most varied embodiments of prosthesis shafts, since a clamping is made at the prosthesis neck which is so strong that a required draw-off force can be produced with this neck support, with the clamping force and the draw-off force being produced by two oppositely moving lever arms, the bending torques of which compensate in regard to the clamping position when equal and opposite forces act at the levers. The apparatus consists of few parts and is simple to sterilize. Experiments have shown that marks arise at the prosthesis necks with the production of the clamping force which reflect the high surface pressing. In this the profile at the rotary bodies is designed such that the product of the clamping force times the friction is always somewhat greater than the required draw-off force. In the event of very large balls the upper edge of the clamping body can grip on directly at the socket of the ball with the rotation of the rotary bodies. In most cases however an intermediate body is preferred which transmits the draw-off forces from the upper edge of the rotary body to the ball.

It is however also possible in accordance with independent claim 2 to transfer the rolling away movement of the profile of the rotary body directly to the housing in the form of a stroke and to draw off the ball with a correspondingly slit housing.

Further improvements of the invention result from the subordinate claims 3 to 14.

If the gap S between the rotary bodies which is provided for the reception of the prosthesis neck contracts in the shape of a V, prosthesis necks with diameters of different sizes can be moved in for drawing off the balls. This can be achieved by a slight conicalness of the rotary bodies in the event of parallel axes of rotation or through a V-shaped arrangement of the axes of rotation and rotary bodies which are cylindrical in the region of the gap S. The latter arrangement has the advantage that equal rotational-angle-dependent relationships for the clamping and the for the lifting of the upper edge arise independently of the diameter of the prosthesis neck. It is therefore sufficient to move up on the neck of the prosthesis with a fork-like intermediate body, to move in below this with the draw-off apparatus, to press both instruments in the direction towards the ball and to actuate the levers in order to cause a clamping and a drawing off at the same time. In short prosthesis necks a separate fork-like intermediate body is advantageous since its limbs can be designed to be very low when they lie transversely to the upper edge of the rotary bodies.

One can however also anchor a fork-like intermediate body movably at the housing, the moving-in slit of which extends parallel to the gap between the rotary bodies. This arrangement has the advantage that no third hand is required to hold the intermediate body and that the operator can draw off the ball without additional help.

If the rotary bodies are arranged in a mirror imaged manner and are connected to one another kinematically in a mirror imaged manner the upper edges of the rotary bodies rise simultaneously and there arises a symmetric stress.

The rotational-angle-dependent theoretical gap reduction of a rotary body is less than the stroke increase of its upper edge to the plane F. They form a ratio between 0.05 and 0.5.

The theoretical reduction of the gap width S which is predetermined by the profiles is adhered to only in a limited manner in that a slight plastic deformation is produced at the prosthesis neck, whereas a portion of the movement practically serves to drive the rotary body and its support apart elastically to such an extent that a required clamping force is produced.

For this reason it is desirable to support the rotary bodies at their outer side with support bodies which project from the housing as bending carriers.

The stroke of the upper edge of the rotary bodies should amount to more than 0.5 mm. A stroke of 3 mm is sufficient for the usual conical connection.

With the draw-off movement the lever arms reduce their spacing so that in the final phase both lever arms can be grasped by one hand in order to produce the maximum required draw-off force.

Figure 4:
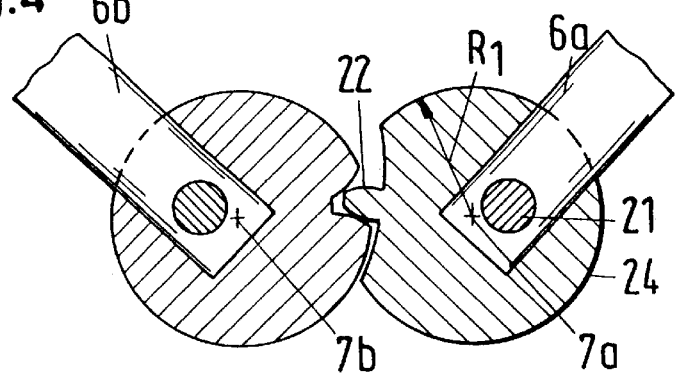
Figure 5:
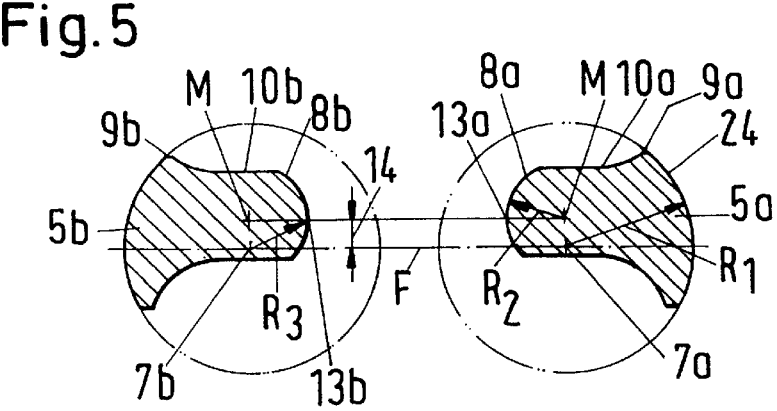
Figure 6:
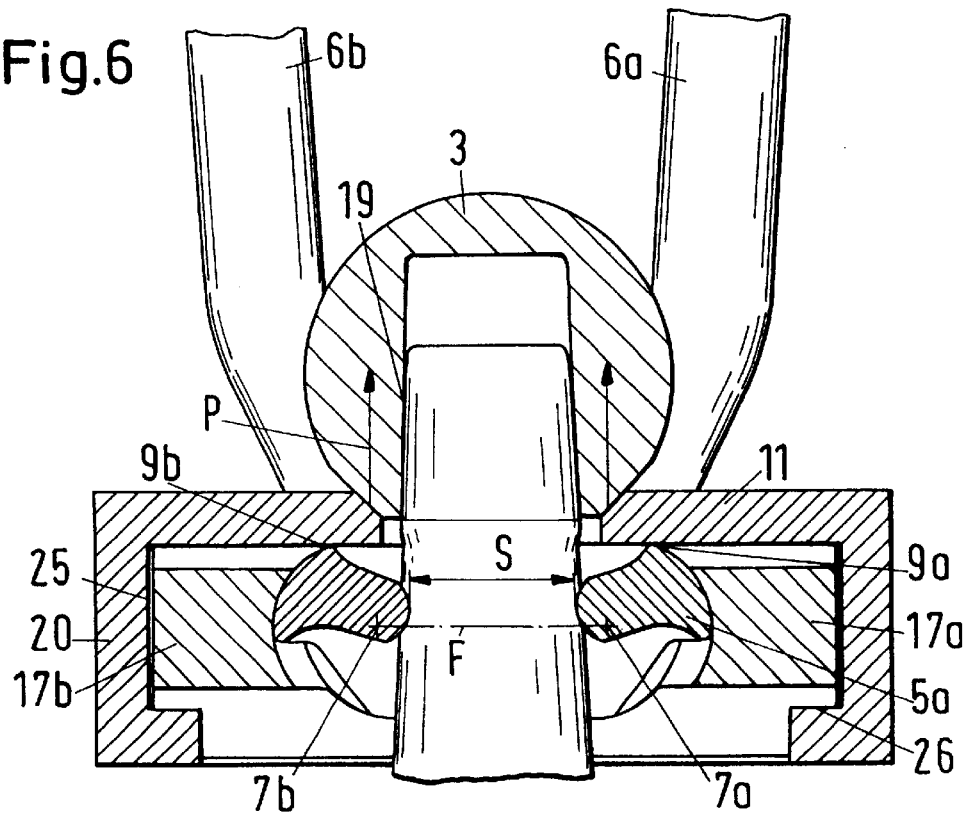

In the following the invention will be explained in detail with reference to exemplary embodiments. Shown are:

FIG. 1 schematically, a view of a ball draw-off apparatus without intermediate body;

FIG. 2 schematically, an enlarged section through a ball draw off apparatus in accordance with FIG. 1 with a separate intermediate body after the placing on of the apparatus onto a prosthesis neck;

FIG. 3 schematically, the arrangement of FIG. 2 during the releasing of the conical connection between the ball and the prosthesis neck;

FIG. 4 schematically, an enlarged section through rotary bodies in accordance with FIG. 1, in which the toothing of the rotary bodies and the anchoring of the lever in the rotary bodies can be seen;

FIG. 5 schematically, an enlarged section through rotary bodies in accordance with FIG. 1 in which the geometrical relationships in the clamping region can be seen;

FIG. 6 schematically, an enlarged section through an arrangement analogous to FIG. 3 in which an intermediate body is held at the housing so as to be movable in the draw-off direction;

FIG. 7 schematically, a further embodiment in which the housing produces a draw-off force directly at the placed on ball with support arms;

FIG. 8 schematically, a section through the arrangement in FIG. 7; and

Figure 9:
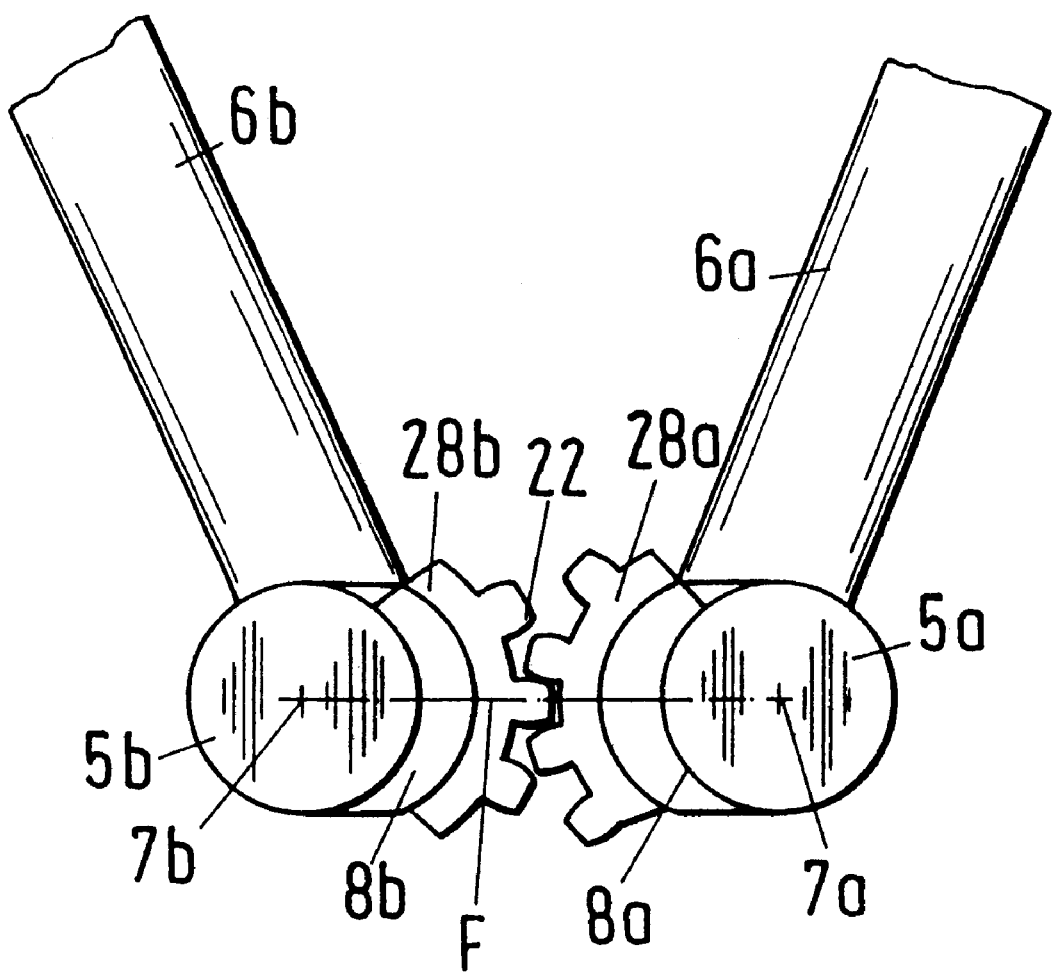

FIG. 9 schematically, a view of the rotary body of FIG. 7 with its toothing.

The invention relates to a ball draw-off apparatus for shaft prostheses with balls 3 which can be placed onto the prosthesis neck 2. The apparatus has two rotary bodies 5*a*, 5*b* which are rotatably supported in a housing 4, which can in each case be rotated with a lever arm 6*a*, 6*b* and which with their axes of rotation 7*a*, 7*b* lie in a common plane and form an open gap S in the projection onto the plane F for the introduction of the prosthesis neck 2. The rotary bodies have a profile which with increasing rotation decreases the gap S for clamping the prosthesis neck 2 and causes an increase of the distance of its upper edge 9*a*, 9*b* from the plane F in order to produce a draw-off force P at the placed on ball 3 directly or indirectly via an intermediate body. Identical reference symbols are used for identical elements in the figures.

An exemplary embodiment is shown in FIGS. 1, 4 and 5 in which two rotary bodies 5*a*, 5*b* are rotatably journalled in a housing 4. The housing has two windows 53, through which in each case a lever arm 6*a*, 6*b* protrudes into the rotary body 5*a*, 5*b* and is anchored there with a securing pin 21. The rotary bodies 5*a*, 5*b* overlap in the region of the lever arms 6*a*, 6*b* and have there a toothing 22 which permits a limited, simultaneous and mirror-imaged rotation of the rotary bodies. The windows 53 are made correspondingly large in the direction of rotation, whereas they secure the rotary bodies which are connected to the lever arms 6*a*, 6*b* in the axial direction of the rotary bodies 5*a*, 5*b*. The rotary bodies lie with a jacket surface 24 which is determined by a radius $R_1$ in contact at the housing 4, so that the housing bores with a radius $R_1$ determine the location of the axes of rotation 7*a*, 7*b* of the rotary bodies 5*a*, 5*b*. The axes of rotation 7*a*, 7*b* lie in a plane F and are slightly opened with respect to one another in the shape of a V in order to form an opening gap S with a cylindrical profile 8*a*, 8*b*, into which prosthesis necks with different diameters can be introduced up to lateral contact at the contact points 13*a*, 13*b*. In FIG. 1 the gap S is drawn at its greatest width, at which the lever arms 6*a*, 6*b* stand apart the furthest and are held through restoring springs 18 in this moving in position, which is provided for the moving in of the prosthesis necks. The rotary bodies 5*a*, 5*b* are supported at their outer side at their jacket surface 24 along the entire length of the gap S through support arms which project out of the housing 4 and which take over as bending springs the pressing forces which are produced during the clamping of the prosthesis and compensate them via the housing. The profiles 8*a*, 8*b* are designed such that the gap S is reduced with the rotating of the rotary bodies 5*a*, 5*b* out of the moved in position and at the same time a rolling away of the profiles 8*a*, 8*b* on the prosthesis neck takes place. The profiles 8*a*, 8*b* have along the rotary bodies 5*a*, 5*b* an upper edge 9*a*, 9*b*, which with the rotation moves upwardly relative to the axis of rotation 7*a*, 7*b* more rapidly than the contact points move downwardly relative to the axis of rotation 7*a*, 7*b*, so that the stroke movement of the upper edge 9*a*, 9*b* in the direction towards the ball is amplified. At very large ball diameters the upper edges 9*a*, 9*b* can grip on directly at the ball in order to produce a draw-off force. For medium and smaller ball diameters it is expedient to arrange a forked intermediate body 11 between the ball and the upper edges 9*a*, 9*b* which transmits the forces to the ball.

In FIG. 5 an example of a profile 8*a*, 8*b* is shown. The rotary bodies 5*a*, 5*b* with axes of rotation 7*a*, 7*b* have on their outer side a piece of jacket surface 24 with radius $R_1$, which rises up to the upper edge 9*a*, 9*b*. The actual roll-away profile 8*a*, 8*b* is determined by a circular section with radius $R_2$, the center M of which is arranged by an amount 14 above the plane F. The contact points 13*a*, 13*b* to the prosthesis neck are accordingly arranged above the plane F. This arrangement has the advantage that the radius $R_3$ of a contact point 13*a*, 13*b* with the axis of rotation 7*a*, 7*b* and the radius $R_2$ of the profile intersect at a selectable angle, which determines the increase of the clamping with the rotation of the rotary bodies 5*a*, 5*b*.

In principle it is also possible to displace the center M into the plane F and to choose the radius of curvature $R_2$ to be greater than $R_3$ in order to achieve a clamping with increasing rotation. The transition from the actual roll-away profile 8*a*, 8*b* to the upper edge 9*a*, 9*b* takes place through an indentation 10*a*, 10*b*.

In FIGS. 2 and 3 is shown the cooperation of a ball draw-off apparatus in accordance with the invention with a separate intermediate body 11 at a prosthesis neck 2 which belongs to a shaft prosthesis 1 or in general to a prosthesis shaft in a tubular bone. In accordance with FIG. 2 an intermediate body 11 in the form of a fork-like instrument 12 is first moved in around the prosthesis neck 2. Then the draw-off apparatus is moved in transversely thereto in its moved in position (lever arms 6*a*, 6*b* apart) and is drawn in the direction towards the ball 3 until on the one hand the limbs of the fork-like instrument 12 lie in contact at the ball 3 and at the upper edges 9*a*, 9*b* of the rotary bodies 5*a*, 5*b* and on the other hand the prosthesis neck 2 lies in contact at the contact points 13*a*, 13*b* in the V-shaped gap S. Then the lever arms 6*a*, 6*b* are moved in the direction towards one another and there arises with the roll-away movement of the profile 8*a*, 8*b* a clamping of the prosthesis neck and an upward movement of the upper edges 9*a*, 9*b* and the fork-like instrument 12 in order to thrust back the ball 3 along its push-on distance, which is pushed on on a cone 19 and is anchored with a shrinking fit, until it is released. In FIG. 3 the ball 3 is released from the cone 19 and can be removed upwardly. The roll-away profile 8*a*, 8*b* still has some reserve for a possible further rotation. The lever arms 6*a*, 6*b*, which are prolonged in grips 16*a*, 16*b* (FIG. 1), lie so close to one another that they can be actuated with one hand in the final phase of the rotation. The radius of curvature $R_2$ of the profile 8*a*, 8*b* is chosen such that no noticeable damage arises at the prosthesis neck 2 during the clamping and the drawing off of the ball.

A further exemplary embodiment is shown in FIG. 6. The clamping and the function of the individual parts are as described in FIG. 1. In contrast to FIG. 1, an intermediate body 11 having an opened slit which extends parallel to the gap S and which is somewhat larger than the gap S is movably secured to the housing. The intermediate piece has side limbs 20 which give it a guiding in the draw-off direction and end abutments 26 which limit its upward movement. The intermediate body is passed around the housing 4 in the manner of a shell in order to take up the torques which are produced at the intermediate body 11 by the draw-off forces P at their distance to the upper edges 9*a*, 9*b*. A clearance 25 of the side limbs 20 from the support arms 17*a*, 17*b* is dimensioned so large that the side limbs do not become stuck in spite of the elastic deformation. In the illustration drawn a large portion of the draw-off movement has already taken place. An advantage of this arrangement is that the surgeon can move the draw-off apparatus with the intermediate body 11 in one direction without help from the outside and can draw off the ball without loosening the prosthesis shaft in the bone.

A further exemplary embodiment, which corresponds to independent claim 2, is shown in FIGS. 7, 8 and 9. For producing the draw-off force P only the roll-away movement of the rotary bodies 5a, 5b, which is transmitted to the housing 4 and the support arms 17a, 17b as a stroke, is used any longer. For this reason the rotary bodies 5a, 5b are surrounded over a greater peripheral angle above all on the upper side. The rotary bodies 5a, 5b likewise have a profile 8a, 8b, which decreases the gap S with increasing rotation, in order to clamp an inserted prosthesis neck and to draw off the ball 3 with the support arms 17a, 17b. The rotary bodies 5a, 5b are inserted into bores of the housing 4 which are arranged in V-shape and are secured with a spectacle frame 28 in their longitudinal direction. Both rotary bodies 5a, 5b have a respective collar 28a, 28b with a toothing 22 which engage into one another in order to produce mirror-imaged movements. At the end of the rotary body, levers 6a, 6b are formed on in order to execute the rotation by hand. The spring action of the support arms 17a, 17b is likewise used for producing a definite clamping force. In order to reduce a "sliding through" of the clamping bodies 5a, 5b before a required clamping force is reached, spring elements 27, such as for example projecting rubber strips, which move resiliently together via a partial stroke before the actual draw-off force P is required, are laid in into the support arms 17a, 17b. In this way a sufficiently large clamping force can at first be built up counter to the abruptly setting in draw-off force.

What is claimed is:

1. Ball draw-off apparatus for shaft prostheses with balls (3) which can be placed onto the prosthesis neck (2), said apparatus having two rotary bodies (5a, 5b) which are rotatably supported in a housing (4), which can in each case be rotated with a lever arm (6a, 6b) and which with their axes of rotation (7a, 7b) lie in a common plane F and form an open gap S in a projection onto the plane F for an introduction of the prosthesis neck (2), with the rotary bodies (5a, 5b) having a profile (8a, 8b) which with increasing rotation decreases the gap S for clamping the prosthesis neck (2) and causes an increase of the distance of an upper edge (9a, 9b) from the plane F in order to produce a draw-off force P at the placed on ball (3) directly or indirectly via an intermediate body.

2. Ball draw-off apparatus for shaft prostheses with balls (3) which can be placed onto the prosthesis neck (2), said apparatus having two rotary bodies (5a, 5b) which are rotatably supported in a housing (4), which can in each case be rotated with a lever arm (6a, 6b) and which with their axes of rotation (7a, 7b) lie in a common plane and form an open gap S and a projection onto the plane F for an introduction of the prosthesis neck (2), with the rotary bodies (5a, 5b) having a profile (8a, 8b) which with increasing rotation decreases the gap S for clamping the prosthesis neck (2) and rolls away on the prosthesis neck (2) in order to produce a draw-off force P at the placed on ball (3) with the housing (4) via support arms (17a, 17b).

3. Apparatus in accordance with claim 1, characterized in that the gap S is open in V shape in order to be able to move in prosthesis necks (2) with diameters of different sizes.

4. Apparatus in accordance with claim 1, characterized in that the axes of rotation (7a, 7b) of the rotary body stand apart in V shape.

5. Apparatus in accordance with claim 1, characterized in that an intermediate body (11) is designed as a separate fork-like instrument (12) which can be pushed on onto the prosthesis neck (2) and which can be moved in a direction towards the ball (3) by both rotary bodies (5a, 5b).

6. Apparatus in accordance with claim 1, characterized in that a fork-like intermediate body (11) which can be pushed on onto the prosthesis neck (2) and which can be moved in a direction towards the ball (3) by both rotary bodies (5a, 5b) is movably anchored at the housing (4).

7. Apparatus in accordance with claim 1, characterized in that the rotary bodies (5a, 5b) are kinematically connected to one another by a toothing (22) in order to execute mirror-image movements with respect to one another.

8. Apparatus in accordance with claim 1, characterized in that a ratio of the gap reduction of a rotary body (5a, 5b) in its projection onto the plane F to a increase of its upper edge relative to the plane F amounts to between 0.05 and 0.5.

9. Apparatus in accordance with claim 8, characterized in that the stroke of the upper edge amounts to more than 0.5.

10. Apparatus in accordance with claim 8, characterized in that in a move-in position for the prosthesis neck (2) the points of contact (13a, 13b) of the rotary bodies (5a, 5b) at the prosthesis neck stand off from the plane F at the prosthesis neck by an amount (14) of less than 6 mm in order to produce a roll away movement of the rotary bodies (5a, 5b) at the prosthesis neck (3) in a framework of an elastic deformation of the rotary bodies (5a, 5b) with their support and of a partly plastic deformation at the prosthesis neck (3).

11. Apparatus in accordance with claim 1, characterized in that the lever arms (6a, 6b) stand further apart during the moving in of the prosthesis neck (2) than in a following rotation of the rotary bodies (5a, 5b).

12. Apparatus in accordance with claim 1, characterized in that the lever arms (6a, 6b) approximately contact one another when a maximally provided stroke (15a, 15b) of the upper edge (9a, 9b) of the rotary bodies (5a, 5b) away from the plane F has been reached.

13. Apparatus in accordance with claim 1, characterized in that the rotary bodies (5a, 5b) are supported through elastically resilient support arms (17a, 17b) which project out of the housing (4) and which determine with a spring action a clamping force which is connected with the an increasing of a profile (8a, 8b).

14. Apparatus in accordance with claim 2, characterized in that spring elements (27) are laid in at the support arms (17a, 17b) which can first be pressed together during the production of a draw-off force P between the ball (3) and the support arms (17a, 17b) in order to produce a greater clamping force during this partial stroke of the housing (4).

* * * * *